United States Patent
Sopori et al.

(10) Patent No.: US 9,234,843 B2
(45) Date of Patent: Jan. 12, 2016

(54) ON-LINE, CONTINUOUS MONITORING IN SOLAR CELL AND FUEL CELL MANUFACTURING USING SPECTRAL REFLECTANCE IMAGING

(75) Inventors: Bhushan Sopori, Denver, CO (US); Przemyslaw Rupnowski, Golden, CO (US); Michael Ulsh, Broomfield, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 14/238,918

(22) PCT Filed: Aug. 25, 2011

(86) PCT No.: PCT/US2011/049111
§ 371 (c)(1),
(2), (4) Date: Feb. 14, 2014

(87) PCT Pub. No.: WO2013/028196
PCT Pub. Date: Feb. 28, 2013

(65) Prior Publication Data
US 2014/0204383 A1    Jul. 24, 2014

(51) Int. Cl.
*G01N 21/55* (2014.01)
*G01N 21/27* (2006.01)
(Continued)

(52) U.S. Cl.
CPC .............. *G01N 21/55* (2013.01); *G01N 21/27* (2013.01); *G01N 21/8901* (2013.01); *G01N 21/898* (2013.01); *G01N 21/9501* (2013.01)

(58) Field of Classification Search
USPC ................. 356/601–635, 237.1; 250/559.03, 250/559.19, 559.21, 484.4, 205
See application file for complete search history.

(56) References Cited

U.S. PATENT DOCUMENTS

| 4,243,473 A | 1/1981 | Yamaguchi et al. |
| 4,329,052 A | 5/1982 | Colombo et al. |

(Continued)

FOREIGN PATENT DOCUMENTS

| JP | 62-119439 | 5/1987 |
| JP | 03-214043 | 9/1991 |

(Continued)

OTHER PUBLICATIONS

Sopori, et al., "Principles and Applications of Reflectometery in PV Manufacturing,", Oct. 2001.
(Continued)

*Primary Examiner* — Sang Nguyen
(74) *Attorney, Agent, or Firm* — John C. Stolpa; Robert G. Pittelkow (57) ABSTRACT

A monitoring system 100 comprising a material transport system 104 providing for the transportation of a substantially planar material 102, 107 through the monitoring zone 103 of the monitoring system 100. The system 100 also includes a line camera 106 positioned to obtain multiple line images across a width of the material 102, 107 as it is transported through the monitoring zone 103. The system 100 further includes an illumination source 108 providing for the illumination of the material 102, 107 transported through the monitoring zone 103 such that light reflected in a direction normal to the substantially planar surface of the material 102, 107 is detected by the line camera 106. A data processing system 110 is also provided in digital communication with the line camera 106. The data processing system 110 is configured to receive data output from the line camera 106 and further configured to calculate and provide substantially contemporaneous information relating to a quality parameter of the material 102, 107. Also disclosed are methods of monitoring a quality parameter of a material.

24 Claims, 9 Drawing Sheets

(51) Int. Cl.
*G01N 21/89* (2006.01)
*G01N 21/898* (2006.01)
*G01N 21/95* (2006.01)

(56) References Cited

U.S. PATENT DOCUMENTS

| | | | |
|---|---|---|---|
| 4,449,818 A | 5/1984 | Yamaguchi et al. | |
| 4,482,245 A | 11/1984 | Makabe et al. | |
| 4,511,800 A | 4/1985 | Harbeke et al. | |
| 4,583,861 A | 4/1986 | Yamaji et al. | |
| 4,614,427 A | 9/1986 | Koizumi et al. | |
| 4,626,101 A | 12/1986 | Ogawa et al. | |
| 4,687,325 A * | 8/1987 | Corby, Jr. | 356/3.09 |
| 4,772,126 A | 9/1988 | Allemand et al. | |
| 4,794,265 A | 12/1988 | Quackenbos et al. | |
| 4,840,487 A | 6/1989 | Noguchi et al. | |
| 4,881,863 A | 11/1989 | Braginsky | |
| 4,885,709 A | 12/1989 | Edgar et al. | |
| 4,923,779 A | 5/1990 | Nelson | |
| 4,925,298 A | 5/1990 | Dobrilla | |
| 4,968,892 A | 11/1990 | McAtee | |
| 4,972,092 A | 11/1990 | Schmitt et al. | |
| 5,008,542 A | 4/1991 | Look et al. | |
| 5,268,749 A | 12/1993 | Weber et al. | |
| 5,334,844 A | 8/1994 | Pollard et al. | |
| 5,365,084 A | 11/1994 | Cochran et al. | |
| 5,367,174 A | 11/1994 | Bazile et al. | |
| 5,406,367 A | 4/1995 | Sopori | |
| 5,455,870 A | 10/1995 | Sepai et al. | |
| 5,490,728 A | 2/1996 | Schietinger et al. | |
| 5,537,203 A | 7/1996 | Carr | |
| 5,581,346 A | 12/1996 | Sopori | |
| 5,586,663 A * | 12/1996 | Graudejus et al. | 209/582 |
| 5,634,267 A | 6/1997 | Farnworth et al. | |
| 5,696,591 A | 12/1997 | Bilhorn et al. | |
| 5,699,447 A | 12/1997 | Alumot et al. | |
| 5,724,268 A | 3/1998 | Sodickson et al. | |
| 5,763,765 A | 6/1998 | Lamont et al. | |
| 5,777,729 A | 7/1998 | Aiyer et al. | |
| 5,796,484 A | 8/1998 | Homma et al. | |
| 5,811,211 A | 9/1998 | Tanaka et al. | |
| 5,999,673 A | 12/1999 | Valentin | |
| 6,064,759 A * | 5/2000 | Buckley et al. | 382/154 |
| 6,154,034 A | 11/2000 | Lovelady et al. | |
| 6,201,261 B1 | 3/2001 | Sopori | |
| 6,275,295 B1 | 8/2001 | Sopori | |
| 6,315,574 B1 | 11/2001 | Kamieniecki et al. | |
| 6,327,374 B1 * | 12/2001 | Piironen et al. | 382/108 |
| 6,369,401 B1 * | 4/2002 | Lee | 250/559.21 |
| 6,393,915 B1 | 5/2002 | Banet et al. | |
| 6,473,062 B1 | 10/2002 | Debiez et al. | |
| 6,532,064 B1 * | 3/2003 | Hearn et al. | 356/237.1 |
| 6,707,958 B2 | 3/2004 | Pering et al. | |
| 6,775,012 B2 * | 8/2004 | Wurz et al. | 356/608 |
| 6,911,350 B2 | 6/2005 | Tsidilkovski et al. | |
| 7,106,077 B2 | 9/2006 | Kaz et al. | |
| 7,177,033 B2 | 2/2007 | Yoshida | |
| 7,179,553 B2 | 2/2007 | Murphy et al. | |
| 7,181,986 B2 | 2/2007 | Roth | |
| 7,190,447 B2 | 3/2007 | Meeks | |
| 7,211,345 B2 | 5/2007 | Hampden-Smith et al. | |
| 7,238,912 B2 | 7/2007 | Sopori | |
| 7,284,411 B2 | 10/2007 | Roth | |
| 7,358,494 B1 | 4/2008 | Gao et al. | |
| 7,362,426 B1 | 4/2008 | Yoo | |
| 7,399,975 B2 | 7/2008 | Harrison | |
| 7,502,119 B2 | 3/2009 | Chalmers et al. | |
| 7,567,351 B2 | 7/2009 | Opsal et al. | |
| 7,635,830 B2 * | 12/2009 | Diederichs | 250/205 |
| 7,664,294 B2 | 2/2010 | Sacher et al. | |
| 7,671,620 B2 | 3/2010 | Manz | |
| 7,687,176 B2 | 3/2010 | Roscoe et al. | |
| 7,729,528 B2 | 6/2010 | O'Dell et al. | |
| 7,815,862 B2 | 10/2010 | Sopori | |
| 2002/0154318 A1 * | 10/2002 | Matsunaga et al. | 356/623 |
| 2002/0166977 A1 * | 11/2002 | Kohda et al. | 250/484.4 |
| 2002/0182333 A1 | 12/2002 | Seaver et al. | |
| 2003/0210394 A1 | 11/2003 | Wei | |
| 2004/0150820 A1 | 8/2004 | Nikoonahad et al. | |
| 2005/0041251 A1 | 2/2005 | Cao et al. | |
| 2005/0196882 A1 | 9/2005 | Steeples | |
| 2005/0264798 A1 | 12/2005 | Nishiyama et al. | |
| 2006/0001430 A1 | 1/2006 | Kepler et al. | |
| 2006/0262320 A1 | 11/2006 | Kawasaki et al. | |
| 2007/0002331 A1 | 1/2007 | Hall | |
| 2007/0002333 A1 | 1/2007 | Ueki et al. | |
| 2007/0024871 A1 | 2/2007 | Maznev | |
| 2007/0059589 A1 | 3/2007 | Arasawa | |
| 2007/0090189 A1 * | 4/2007 | Suwa et al. | 235/454 |
| 2007/0109540 A1 | 5/2007 | Maznev | |
| 2007/0229847 A1 | 10/2007 | Indars et al. | |
| 2007/0231930 A1 | 10/2007 | Funk et al. | |
| 2007/0259256 A1 | 11/2007 | Le Canut et al. | |
| 2007/0274447 A1 | 11/2007 | Mazor et al. | |
| 2008/0026294 A1 | 1/2008 | Jiang | |
| 2008/0028860 A1 | 2/2008 | Refko et al. | |
| 2008/0042654 A1 | 2/2008 | Kato | |
| 2008/0055591 A1 * | 3/2008 | Walton | 356/237.1 |
| 2008/0062422 A1 | 3/2008 | Thomas et al. | |
| 2008/0118783 A1 | 5/2008 | Cetegen et al. | |
| 2008/0150540 A1 | 6/2008 | Okuda | |
| 2008/0151237 A1 | 6/2008 | Lian et al. | |
| 2008/0165924 A1 | 7/2008 | Wang et al. | |
| 2008/0197857 A1 | 8/2008 | Shin | |
| 2008/0198366 A1 | 8/2008 | LeBlanc | |
| 2008/0280374 A1 | 11/2008 | Potyrailo et al. | |
| 2009/0126779 A1 | 5/2009 | Heeger et al. | |
| 2009/0128830 A1 | 5/2009 | Kottler et al. | |
| 2009/0180112 A1 | 7/2009 | Wang | |
| 2009/0262323 A1 | 10/2009 | Sasaki | |
| 2009/0284734 A1 | 11/2009 | Tang et al. | |
| 2009/0291295 A1 | 11/2009 | Chung et al. | |
| 2009/0310745 A1 | 12/2009 | Banchet et al. | |
| 2009/0319225 A1 | 12/2009 | Mansfield | |
| 2010/0171959 A1 | 7/2010 | Walsh | |
| 2010/0195114 A1 * | 8/2010 | Mitsumoto et al. | 356/601 |
| 2010/0239157 A1 | 9/2010 | O'Dell et al. | |
| 2010/0290055 A1 | 11/2010 | Kim et al. | |
| 2010/0292936 A1 | 11/2010 | Jepsen | |
| 2011/0089348 A1 * | 4/2011 | Finarov et al. | 250/559.39 |
| 2011/0244588 A1 | 10/2011 | Maity et al. | |
| 2011/0299094 A1 | 12/2011 | Dillon et al. | |
| 2012/0133913 A1 | 5/2012 | Okita | |
| 2014/0078514 A1 | 3/2014 | Zhu | |
| 2014/0093985 A1 | 4/2014 | Li et al. | |
| 2014/0204383 A1 | 7/2014 | Sopori | |

FOREIGN PATENT DOCUMENTS

| | | |
|---|---|---|
| JP | 2005038694 | 2/2005 |
| JP | 2005134218 | 5/2005 |
| WO | WO 2011028807 | 3/2011 |
| WO | WO 2011042606 | 4/2011 |

OTHER PUBLICATIONS

Sopori, "Reflectance Spectroscopy: Rapid Quantitative Measurements in Commercial Production of SI Solar Cells,", Jan. 2005.
Kini, et al., "Effect of Bi alloying on the hole transport in the dilute bismide ally GaAs1-xBix," Physical Review B, vol. 83, Issue 7, Feb. 2011, pp. 075307-1-075307-6.
PCT Patent Application No. PCT/US211/49111dated Dec. 13, 2011.
Aieta et al., "Applying infrared thermography as a quality-control tool for the rapid detection of polymer-electrolyte-membrane-fuel-cell catalyst-layer-thickness variations", Journal of Power Sources, vol. 211, Feb. 20, 2012, pp. 4-11.
Bayro-Corrochano, "Review of Automated Visual Inspection 1983-1993 Part I: conventional approaches", Proc. SPIE vol. 2055, Intelligent Robots and Computer Vision XII, Aug. 20, 1993, pp. 128-158.
Cele, "Preparation and Characterization of Nafion-Based Nonocomposite Membranes for Fuel Cell Applications", A thesis submitted to the Faculty of Science and Agriculture; University of Zululand, 2010, pp. 1-195.

(56) References Cited

OTHER PUBLICATIONS

Hesler, "A study of the surface roughness of the NafionTM membrane in a PEM Fuel Cell", A Major Qualifying Project Report: Submitted to the Faculty of Worcester Polytechnic Institute, Apr. 2009, pp. 1-29.

"NREL Develops Technique to Measure Membrane Thickness and Defects in Polymer Electrode Membrane Fuel Cells", Nov. 15, 2010, pp. 1.

Ojanen, et al., "Spectral irradiance model for tungsten halogen lamps in 340-850 nm wavelength range", Applied Optics, vol. 49, No. 5, Feb. 10, 2010, pp. 880-886.

Stanfield, "Metrology for Fuel Cell Manufacturing", Jun. 13, 2008.

Stanfield, "Metrology for Fuel Cell Manufacturing", Jun. 12, 2010.

Stanfield, et al., "Metrology for Fuel Cell Manufacturing", May 12, 2011.

Stanfield, et al., "Metrology for Fuel Cell Manufacturing", May 16, 2012.

Sopori, B. "A New Defect Etch for Polycrystalline Silicon", Journal of Electrochemical Society: Solid-State Science and Technology, vol. 131, Issue 3, 1984, pp. 667-672.

Sopori, B. "Principle of a new reflectometer for measuring dielectric film thickness on substrates of arbitrary surface characteristics", Review Science Instruments, vol. 59, Issue 5, May 1988, pp. 725-727.

Sopori, B. "Use of optical scattering to characterize dislocations in semiconductors", Applied Optics, vol. 27, Issue 22, Nov. 15, 1988, pp. 4676-4683.

Takeshi et al., JP 2005038694, "Inspection Method of MEA for polymer Electrolyte Fuel cell (Machine Translation for JP 2005038694", Feb. 10, 2005, pp. 16.

Ulsh, M., et al., "Fuel Cell Membrane Electrode Assembly Manufacturing R&D", NREL, FY10 Annual Progress Report, DOE Hydrogen Program, Jun. 15, 2010, pp. 1127-1130.

PCT/US11/49111 International Search Report dated Dec. 13, 2011.

PCT/US11/49111 Written Opinion dated Dec. 13, 2011.

Stanfield, E., "VI.3 Metrology for Fuel Cell Manufacturing", FY 2008 Annual Progress Report, DOE Hydrogen Program, pp. 1098-1104.

* cited by examiner

ON-LINE, CONTINUOUS MONITORING IN SOLAR CELL AND FUEL CELL MANUFACTURING USING SPECTRAL REFLECTANCE IMAGING

CONTRACTUAL ORIGIN

The United States Government has rights in this invention under Contract No. DE-AC36-08GO28308 between the United States Department of Energy and the Alliance for Sustainable Energy, LLC, the manager and operator of the National Renewable Energy Laboratory.

BACKGROUND

Semiconductor wafers are used for a variety of purposes in the semiconductor, solar energy and other industries. Wafer quality often depends on variables such as thickness and surface characteristics. Poor quality wafers may have uneven thickness or uneven surface characteristics; whereas, higher quality wafers will have substantially uniform thickness and substantially uniform surface characteristics. In the semiconductor industry, wafers are used as a substrate supporting the fabrication of all types of semiconductor devices. Therefore, wafer quality can crucially influence the mechanical and/or electronic yield of wafer-based semiconductor device circuits. Accordingly, several techniques have been developed for wafer quality assessment and monitoring.

Fuel cells using proton exchange membranes (PEM) have gained considerable acceptance for automotive and portable power needs. It is expected that the fuel cell market will grow rapidly in the future. As this growth occurs, the fuel cell industry will also require monitoring techniques that are fast, non-destructive, and capable of high throughput. Such monitoring will be beneficial for membranes, electrode coatings, gas diffusion layers, others layers, surfaces or structures. The membrane properties that could be monitored include, but are not limited to, catalyst distribution and loading, electrode structure and porosity, thickness, membrane uniformity and defects, extent of curing, gas diffusion layer porosity, surface structure, and hydrophobicity.

Silicon wafers and fuel cell membranes are significantly different structures. Nonetheless, the monitoring of selected quality parameters in a continuous production environment would be advantageous for both wafer based device and fuel cell production.

A reflectometer may be used to measure selected physical characteristics of a semiconductor wafer or fuel cell membrane including but not limited to surface roughness, surface texture, crystalline grain orientation, antireflection coating thickness, wafer thickness, metallization characteristics and other parameters noted above. Reflectometer measurements are most typically used for wafer characterization before or after various steps in solar cell fabrication. In addition, a reflectometer can be used to measure certain membrane parameters, for example the thickness of fuel cell membranes or the detection and recognition of membrane defects. It is important to note however, that a typical reflectometer system is implemented in a static manner. Thus, a reflectometer based device is configured to measure one sample at a time. A typical reflectometer based system requires that a test wafer or a sample from a fuel cell membrane to be placed into an off-production line measurement chamber and then held stationary during optical examination. Thus, reflectometer based systems are best suited for process control where process monitoring is done by periodic sampling rather than continuous monitoring.

The solar cell fabrication industry is beginning to rely exclusively upon automated conveyor belt transport of wafers between processing steps. Generally, an array of wafers move through the processing apparatus more or less continuously leaving little or no opportunity for periodic sampling with a reflectometer. Thus, there exists a need to develop new continuous surface examination techniques to meet evolving industry requirements. Fuel cell membranes are also fabricated by performing various steps on a continuously moving web line. Thus, as the fuel cell industry grows, there is need to develop new techniques for monitoring selected membrane parameters on the web line itself, without stopping or slowing production.

The foregoing examples of the related art and limitations related therewith are intended to be illustrative and not exclusive. Other limitations of the related art will become apparent to those of skill in the art upon a reading of the specification and a study of the drawings.

SUMMARY OF THE EMBODIMENTS

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One embodiment is a monitoring system comprising a material transport system providing for the transportation of a substantially planar material through the monitoring zone of the monitoring system. The system also includes a line camera positioned to obtain multiple line images across a width of the material as it is transported through the monitoring zone. The system further includes an illumination source providing for the illumination of the material transported through the monitoring zone such that light reflected in a direction normal to the substantially planar surface of the material is detected by the line camera. A data processing system is also provided in digital communication with the line camera. The data processing system is configured to receive data output from the line camera and further configured to calculate and provide substantially contemporaneous information relating to a quality parameter of the material.

The substantially planar material may be a semiconductor wafer, a fuel cell membrane or similar material having a substantially planar surface.

The illumination source may be of any suitable configuration, including but not limited to a light source in communication with an optical fiber providing for the transmission of light from the light source to a rectangular aperture and a lens in optical communication with the rectangular aperture. The illumination source could alternatively be implemented with a linear array of LEDs or a linear lamp and parabolic reflector providing for the projection of light toward the substantially planar material. Illumination may also be provided by more than one light source, in particular by more than one symmetrically located light source.

In one embodiment, the system collects data from diffusely reflected light. Thus, the illumination source is positioned with respect to the substantially planar material such that a line from the illumination source to the planar material forms an angle of less than 90° and preferably less than 45° with the planar surface of the planar material. In another embodiment, best suited to implementations where the substantially planar material is a fuel cell membrane, the illumination source is located opposite the substantially planar material from the line camera and thus projects light through the material which is then detected by the line camera.

The illumination source may include a source of polychromatic light having a range of wavelengths. In certain instances it is desirable to collect data from the material while under monochromatic illumination or at specific wavelengths. Therefore, the monitoring system may further comprise an optical filtering system associated with one or both of the line camera and illumination source configured to obtain line data at selected monochromatic wavelengths.

The data processing system is configured to provide substantially contemporaneous data output regarding at least one of the following wafer quality parameters; material surface roughness, material texture etch quality, anti-reflection coating thickness, wafer thickness, metallization quality, material back reflectance back layer thickness, crystalline grain size and crystalline grain orientation or at least one of the following membrane quality parameters; material surface roughness, thickness values for different layers of a multiple-layer membrane, thickness of a single layer membrane, variations in the porosity of the electrode-coated membrane, presence of absorbing defects, or presence of non-opaque defects.

The monitoring system may further include a triggering device which causes a line of data to be obtained at selected intervals by the line camera. The triggering device may be, but is not limited to an edge sensor, a position encoder or a time regulator.

An alternative embodiment is a method of monitoring a material. The method comprises the steps of transporting a substantially planar material through the monitoring zone of a monitoring system, obtaining multiple line images across a width of the material transported through the monitoring zone with a line camera, illuminating the material transported through the monitoring zone such that light reflected or transmitted in a direction normal to the substantially planar surface of the material is detected by the line camera and calculating a quality parameter of the material with a data processing system in digital communication with the line camera.

The method may further include comparing the calculated quality parameter of the material with a known standard parameter and identifying an irregularity in the material based upon the calculated quality parameter.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise The embodiments disclosed herein relate to methods and apparatus for the high throughput monitoring of semiconductor wafers, solar cells, and thin membranes such as fuel cell membranes. Generally, the screening of wafers and membranes is based upon the detection and analysis of light scattered from a wafer or membrane surface. Alternatively, transmitted or both reflected and transmitted light may be detected and analyzed to screen a relatively thin membrane or other transmissive substrate.

Monitoring System

Figure 1:
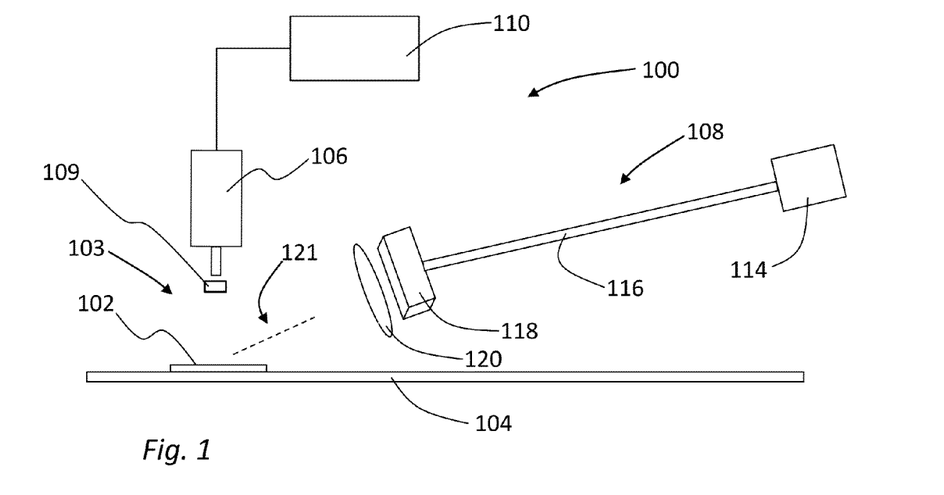
FIG. 1 is a schematic diagram of a monitoring system embodiment.
Figure 2:
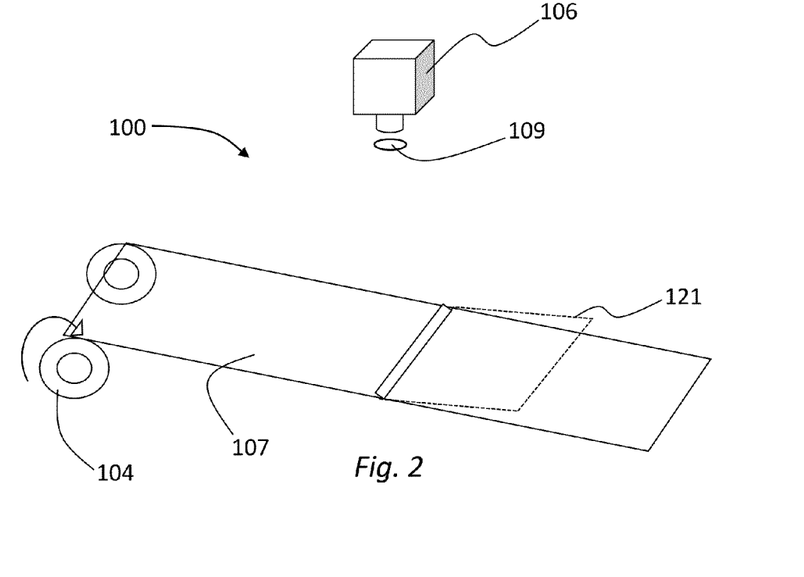
FIG. 2 is a schematic diagram of an alternative embodiment of a monitoring system.

The schematic diagram of FIG. 1 shows one embodiment of a monitoring system 100 configured to implement the methods disclosed herein. The monitoring system 100 includes a material transport system providing for the transport of a substantially planar material through a monitoring zone. In particular, the substantially planar material can be at least one, but typically many semiconductor wafers 102 transported through the monitoring zone 103. The material transport system will typically be a conveyor belt 104 as illustrated in FIG. 1 if the system 100 is configured to monitor the processing of wafers 102. Alternatively, the substantially planar material could be a fuel cell membrane and the material transport system could be the rollers and supports associated with a membrane processing web line as illustrated in FIG. 2.

The monitoring system 100 also includes a line camera 106 positioned to obtain a series of substantially line images across a width of the wafer 102 or membrane 107 (FIG. 2) as the wafer or membrane is transported through the monitoring zone 103. Specific attributes of a suitable line camera 106 are described in detail below.

The monitoring system 100 further includes one or more illumination sources 108 providing for the illumination of the material transported through the monitoring zone 103 such that a component of the light reflected from the substantially planar surface of a wafer or membrane can be detected by the line camera 106. In alternative embodiments, light transmitted through the material may be detected. The system 100 also includes a data processing system 110 in digital communication with the line camera output and configured to calculate and provide substantially contemporaneous data output relevant to a quality parameter of the material being monitored. Each of these elements of the system 100 is described in detail below.

An important attribute of the monitoring system 100 is the ability to monitor each wafer 102 or membrane section in real time as the wafer or membrane is transported through the system at production speeds. Most known image analysis techniques typically rely upon the extraction of useful data from a two dimensional image. Thus, under conventional techniques, an image is obtained, processed and data is extracted over the entire imaged area. Accordingly, conventional image based monitoring solutions take time and are best suited to the detailed analysis of selected samples in a batch of wafers. The monitoring system 100 may be configured to continuously process each line of data captured by the line camera as described below. Therefore in selected embodiments it is not necessary to stop or slow production or to store or display images for analysis, thereby freeing up system resources and facilitating real time monitoring.

The methods disclosed herein can be used to monitor numerous characteristics of a wafer or membrane, including but not limited to, surface conditions resulting from wafer sawing, the wafer texture or etching quality, grain orientation or grain size distribution within a wafer, wafer thickness, wafer or membrane antireflection coating thickness, metallization area and metallization height. The disclosed methods can be used to perform a final cell "visual test."

Figure 3:
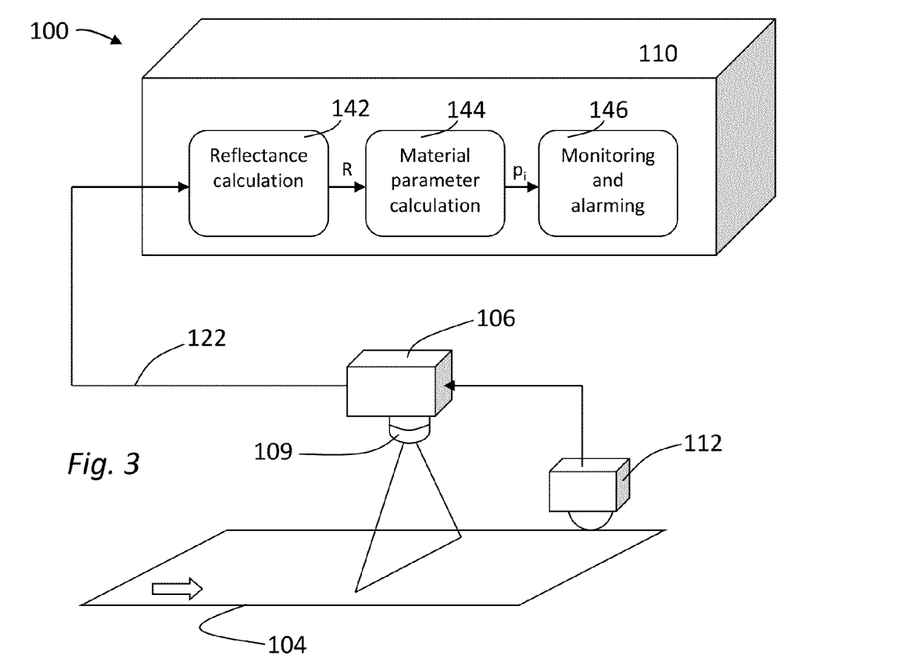
FIG. 3 is a schematic diagram of an alternative embodiment of a monitoring system.

The monitoring system 100 uses a line camera 106 to obtain reflectance or transmittance data which may be processed to determine selected wafer of membrane characteristics or parameters. As illustrated in FIG. 3, the data obtained from the line camera 106 will typically be synchronized to a relevant wafer or web line location by an encoder 112 associated with the conveyor belt 104 or web line. If the wafer or membrane is moving at a constant speed, the line camera could also be synchronized to a time regulated optical or mechanical trigger that initiates data collection. Alternatively, the line camera could be triggered by an edge-sensor positioned to sense the leading and trailing edges of wafers on a conveyor.

The monitoring system can be implemented with one or more than one line cameras 106. For example a linear array of line cameras could be implemented across a web line 107 or conveyor 104 to acquire data from a relatively wider membrane or a wide array of wafers. There are numerous line camera systems commercially available that are suitable for implementing the described embodiments. One possible system suitable for the implementation of the described apparatus and methods is a Dalsa HS-SO-12K40 HSLink, having a linear resolution of 12000 pixels. This particular camera can detect at the rate of 34,000 frames per second which corresponds to a conveyor speed of $25 \times 34 \times 10^3$ μm/s or about 0.08 m/s By definition a line camera acquires data in a format of one line at a time. A typical line camera may have 12000 pixels per line with a 5 μm pixel size thus presenting a 6 cm actual length imaging line. A typical wafer has a width of 6 inches. Thus, the camera when placed a suitable distance above the wafer or membrane and provided with appropriate focusing optics, may have a linear resolution across a 6 inch wafer of about 12 μm or a resolution of about 25 μm across a 12 inch wide fuel cell membrane. The encoder 112 or other triggering element may be configured to generate a trigger signal at appropriate intervals relative to the conveyor or web line speed or position to generate a lengthwise resolution to match the resolution across the wafer or membrane width. For example, the lengthwise resolution may be controlled to be 12 μm for the wafer example above and 25 μm for the membrane example, based upon the trigger timing and conveyor speed. The foregoing resolutions are representative only; any suitable width or length resolution can be achieved with appropriate optics and spacing between the camera and the imaged surface plus control over the conveyor or web line speed and triggering interval.

The system 100 also includes an illumination source 108 to illuminate the portion of the wafer or membrane being transported through the monitoring zone 103. As illustrated in FIG. 1, the illumination source 108 may include a lamp 114. The lamp may be a tungsten lamp, one or more LEDs, a gas discharge lamp or any other suitable light generating device. In the embodiment of FIG. 1, light energy from the lamp is conveyed to the monitoring zone in a fiber optic cable 116. The fiber optic cable 116 may be configured to terminate in a relatively small rectangular aperture 118 and the light emanating from the aperture may be focused by a lens such as a cylindrical lens 120 or other suitable means into a substantially linear illumination source. It is desirable that the illumination source create an even intensity zone across the portion of the wafer or membrane passing through the monitoring zone. For example, the even intensity illumination zone may be as wide as the conveyor or web line. The length of the illumination zone in the direction of material transport is relatively unimportant.

Light which is reflected or scattered off of the wafer or web line surface in a direction normal to the surface can be detected by the line camera. Thus, the material is preferably illuminated by an illumination beam 121 projected, as shown in FIG. 1 and FIG. 2, at a shallow angle to a plane defined by the wafer surface or web line. The light projection angle is ideally 90° or 45° or less with respect to the planar surface of the material being examined. Therefore, although a membrane or wafer typically has a highly polished surface, the light detected by the line camera is not light reflected in a specular manner from the surface. The placement of the illumination source at an angle of less than 90° with respect to the plane of the sample assures that any specular reflection is reflected away from the camera.

One or more additional illumination sources can be used in the system. For example, in the FIG. 1 embodiment, an illumination source corresponding to illumination source 108 could be placed symmetrically opposite source 108.

As noted above, it may be advantageous to provide a substantially linear light beam at the monitoring zone that illuminates the wafer or membrane in a relatively narrow band across the direction of wafer or membrane transport. Thus, a substantially linear illumination source would illuminate the wafer or membrane in a strip parallel to the orientation of the line camera pixels. A linear illumination source could be provided with a wide rectangular fiber optic bundle optically communicating with a light energy source, with a linear array of LEDs, with a linear lamp having a back reflector or by other means.

The illumination source 108 may provide polychromatic illumination. Certain material quality parameters are best calculated using data collected at selected monochromatic wavelengths. Thus, the illumination source 108 or the line camera 106 may also include one or more optical filters 109 providing for the capture of data at selected wavelengths.

Figure 4:
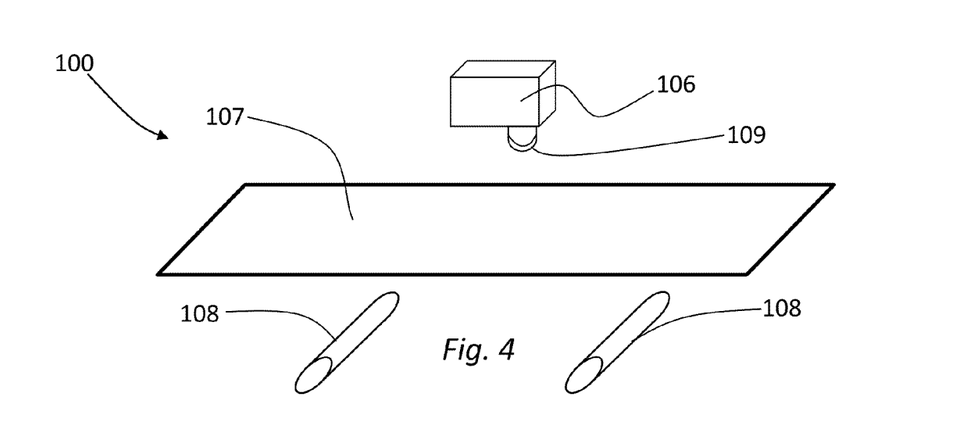
FIG. 4 is a schematic diagram of an alternative embodiment of a monitoring system.

Alternatively, a system 100 may be configured so the illumination source transmits light through the material being monitored, typically a membrane web line. For example, as shown in FIG. 4, one or more linear illumination sources 108 may be positioned opposite the web line 107 from a line camera 106 such that light transmitted through the web line is detected by the camera.

Figure 5:
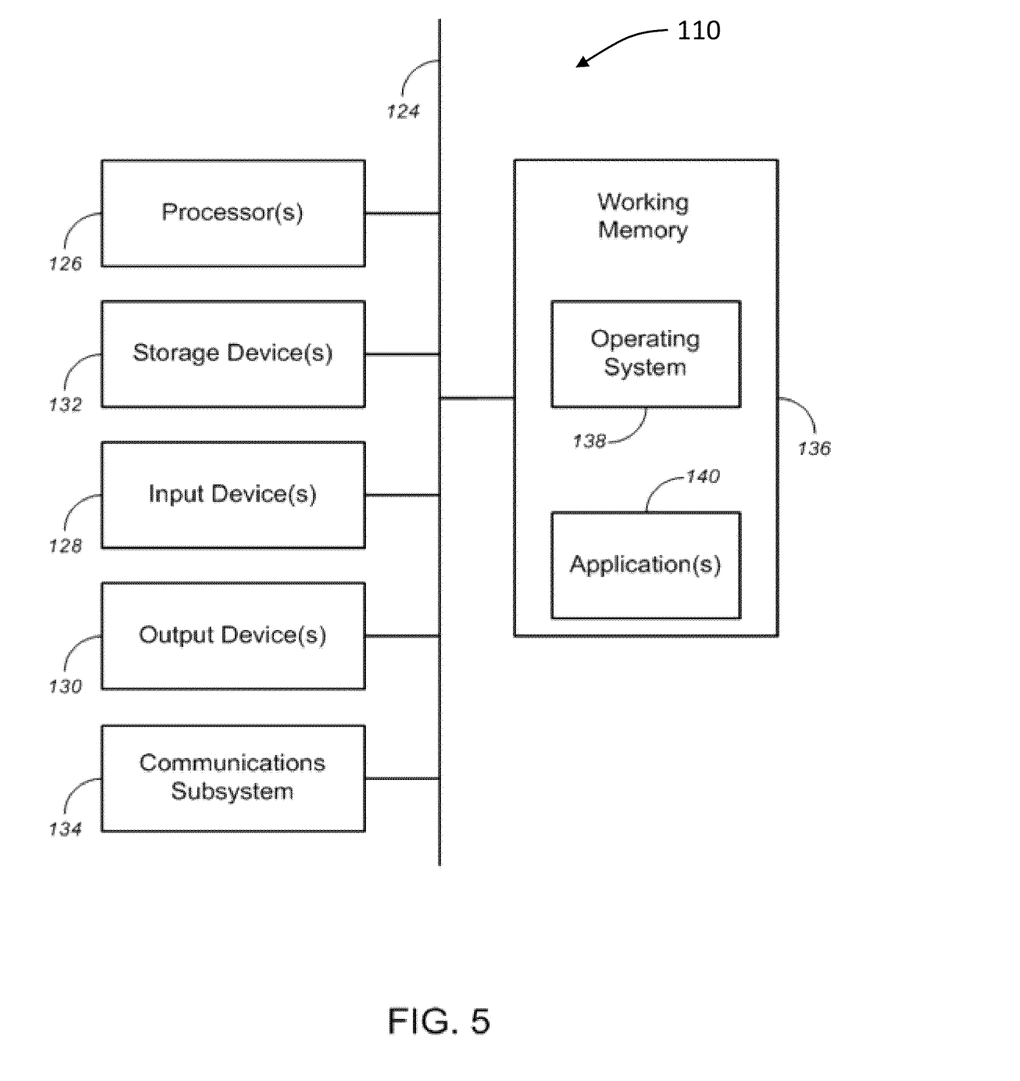
FIG. 5 is a functional block diagram representation of the data processing system associated with a monitoring system.

As shown in FIG. 3, an unprocessed digital output signal 122 may be read from the line camera 106 and provided to a data processing system 110. The signal 122 may be conveyed from the line camera 106 electronically in a suitable data cable or wirelessly. Alternatively, the signal 122 may be conveyed by digital optic means in a suitable fiber optic cable. FIG. 5 provides a schematic illustration of one embodiment of a data processing system 110 configured to perform the methods provided by various embodiments, as described herein. It should be noted that FIG. 5 is meant only to provide a generalized illustration of various components, of which one or more (or none) of each may be utilized as appropriate. FIG. 5 therefore, broadly illustrates how individual system elements may be implemented in a relatively separated or relatively more integrated manner.

The data processing system 110 is shown comprising hardware elements that can be electrically coupled via a bus 124 (or may otherwise be in communication, as appropriate). The hardware elements may include one or more processors 126, including without limitation one or more general-purpose processors and/or one or more special-purpose processors (such as digital signal processing chips, graphics acceleration processors, and/or the like); one or more supplemental input devices 128, which can include without limitation a mouse, a keyboard and/or the like; and one or more output devices 130, which can include without limitation a display device, a printer and/or the like.

The data processing system 110 may further include (and/or be in communication with) one or more storage devices 132, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The data processing system 110 might also include a communications subsystem 134, which can include without limitation a modem, a network card (wireless or wired), an infrared communication device, a wireless communication device and/or chipset (such as a Bluetooth™ device, an 802.11 device, a WiFi device, a WiMax device, a WWAN device, cellular communication facilities, etc.), and/or the like. The communications subsystem 134 may permit data to be exchanged with a network (such as the network described below, to name one example), with other computer systems, and/or with any other devices described herein. In many embodiments, the data processing system 110 will further comprise a working memory 136, which can include a RAM or ROM device, as described above.

The data processing system 110 also may comprise software elements, shown as being currently located within the working memory 136, including an operating system 138, device drivers, executable libraries, and/or other code, such as one or more application programs 140, which may comprise computer programs provided by various embodiments, and/or may be designed to implement methods, and/or configure systems, provided by other embodiments, as described herein. Merely by way of example, one or more procedures described with respect to the method(s) discussed below might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 132 described above. In some cases, the storage medium might be incorporated within a computer system, such as the data processing system 110. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the data processing system 110 and/or might take the form of source and/or installable code, which, upon compilation and/or installation on the data processing system 110 (e.g., using any of a variety of generally available compilers, installation programs, compression/decompression utilities, etc.) then takes the form of executable code.

The terms "machine readable medium" and "computer readable medium," as used herein, refer to any medium that participates in providing data that causes a machine to operation in a specific fashion. In an embodiment implemented using the data processing system 110, various computer readable media might be involved in providing instructions/code to processor(s) 126 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 132. Volatile media includes, without limitation, dynamic memory, such as the working memory 136. Transmission media includes, without limitation, coaxial cables, copper wire and fiber optics, including the wires that comprise the bus 124, as well as the various components of the communication subsystem 134 (and/or the media by which the communications subsystem 134 provides communication with other devices). Hence, transmission media can also take the form of waves (including without limitation radio, acoustic and/or light waves, such as those generated during radiowave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Returning to FIG. 2, the data processing system 110 includes software and hardware elements that perform a reflectance calculation 142 as described below. The reflectance calculation 142 is analyzed to extract a material parameter calculation. Based upon the material parameter calculation, the computer system may provide for contemporaneous monitoring of an assembly line of wafers or a membrane web line and issue an irregularity alarm 146 if required.

Signal Processing

As noted above, the line camera 106 provides a data signal generated by reflected or transmitted light from the width of the wafer of membrane passing through the monitoring zone. The line camera may acquire a line of data upon receipt of a trigger from an encoder 112, from a detected feature such as a wafer edge or based upon a fixed or variable clock signal. An encoder signal digitally associates a linear image with a location on a wafer or membrane. Thus, the output of the camera may comprise a signal in the form of ($R_{ij}$, $x_i$, $y_j$).

The line camera 106 and data processing system 110 may be configured to acquire and process data in at least two separate modes, including but not limited to an image storage mode and a monitoring mode. In an image storage mode, the reflectance image of a wafer/cell or a segment of a web line can be stored line by line in a storage buffer. This series of linear data sets can then be transformed into a parameter image or stored as a motion picture type image of the moving object. The primary objective of image storage is to save image data for later examination. A system operating in an image storage mode would be useful in preliminary investigations, for example during the optimization of a production line or for research and development applications.

Alternatively, a line camera 106 and data processing system 110 may be configured to continuously monitor a production line of wafers or a membrane web line. In a monitoring mode, the primary objective is to continuously compare the acquired parameter signal with selected parameter values and then save only the data that exhibits deviation from expected parameter values. In addition a continuous monitoring mode may provide an alarm upon the occurrence of a deviation or otherwise alert an operator if irregularities occur.

Figure 6:
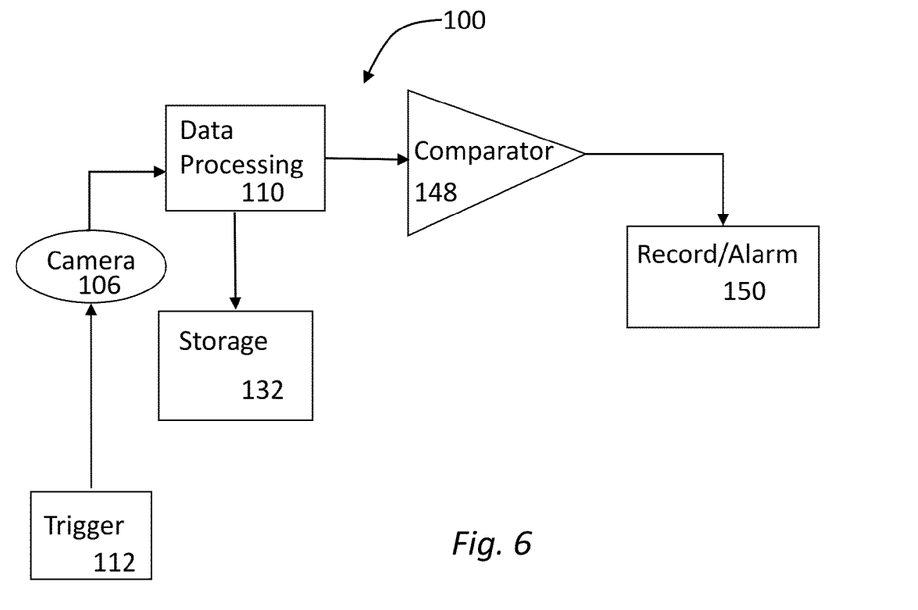
FIG. 6 a functional block diagram representation of a monitoring system.
Figure 7:
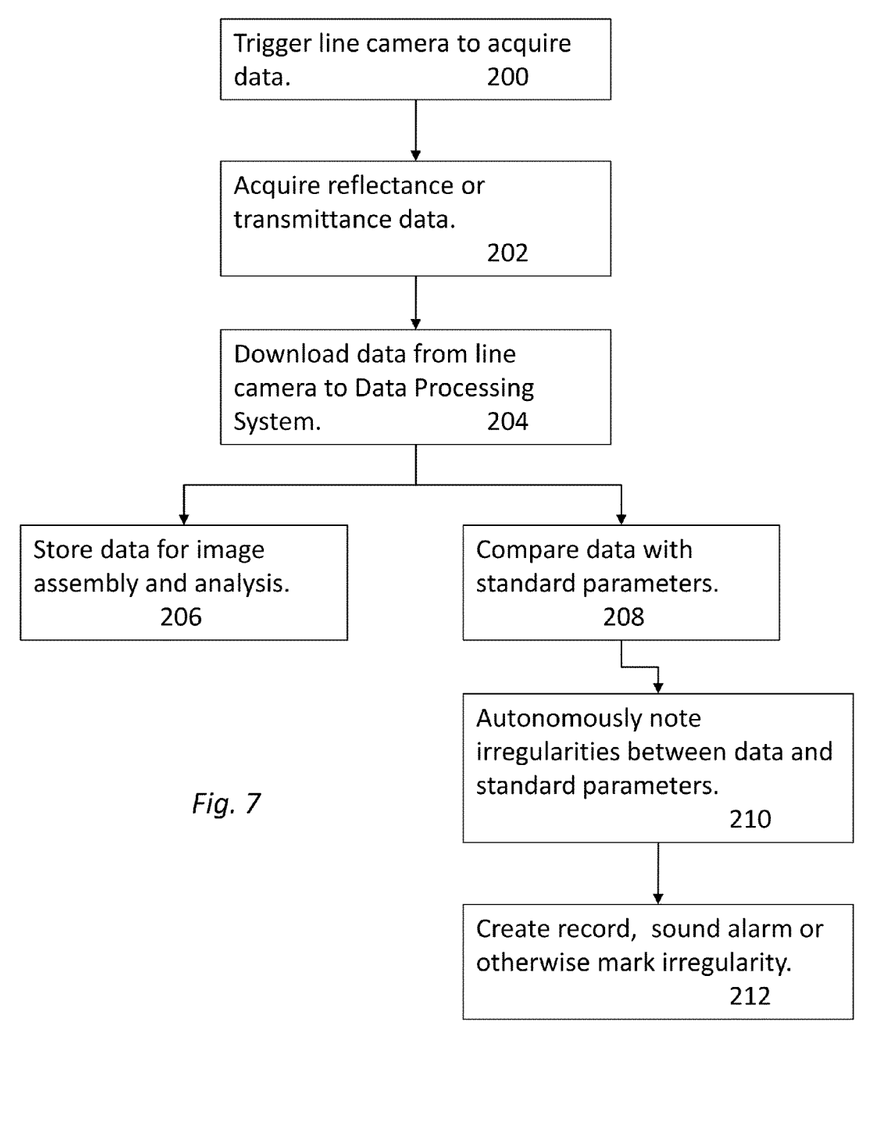
FIG. 7 is a flowchart representation of a method embodiment.

For example, as shown in FIGS. 6 and 7 a system 100 may include a line camera 106 that acquires reflectance or transmittance data across a moving wafer or membrane at a specific point in time in response to a trigger generated by a position encoder 112 (steps 200 and 202). The data generated by the line camera 106 may be downloaded to a data processing system 110 having storage 132 (step 204). The data processing system 110 may be configured to store the data associated with each image line and optionally assemble the lines into a two dimensional reflectance image that can be analyzed at any time (step 206). Alternatively, the data processing system 110 may be configured to compare each line of data with standard parameters through comparator logic 148 (step 208). The standard parameters may be calculated by dynamically averaging data obtained from each line and comparing each new line of data with the average. Thus irregularities will be quickly noted (step 210). The comparator logic may further be configured to create a record 150, sound an alarm or otherwise note an irregularity along with position information directly from the encoder 112 or calculated based upon a regular clock or physical trigger.

Solar Cell Process Monitoring

As noted above, various wafer parameters may be monitored using the embodiments disclosed herein. These parameters include but are not limited to surface roughness, surface texture or etch quality, anti-reflection coating thickness, wafer thickness, metallization, back layer thickness, crystalline grain size and crystalline grain orientation. It may be necessary to use conventional optical filters 109 or specific wavelength illumination sources to monitor at various wavelengths to best detect variations in the above parameters. A list of preferred wavelengths and a range of usable wavelengths for selected parameters is set forth in Table 1 below:

TABLE 1

| Parameter | Preferred Wavelength | Suitable Wavelengths |
|---|---|---|
| Surface roughness | $\lambda = 0.4$ µm | $0.4$ µm $< \lambda < 0.6$ µm |
| Texture-etch quality | $\lambda = 0.4$ µm | $0.4$ µm $< \lambda < 0.6$ µm |
| AR coating thickness | $\lambda = 0.8$ µm | $0.8$ µm $< \lambda < 0.9$ µm |
| Wafer thickness | $\lambda = 1.05$ µm | $1.0$ µm $< \lambda < 1.1$ µm |
| Metallization | $\lambda = 1.05$ µm | $1.0$ µm $< \lambda < 1.1$ µm |
| Back reflectance | $\lambda = 1.05$ µm | $1.2$ µm $< \lambda < 1.5$ µm |

Figure 8:
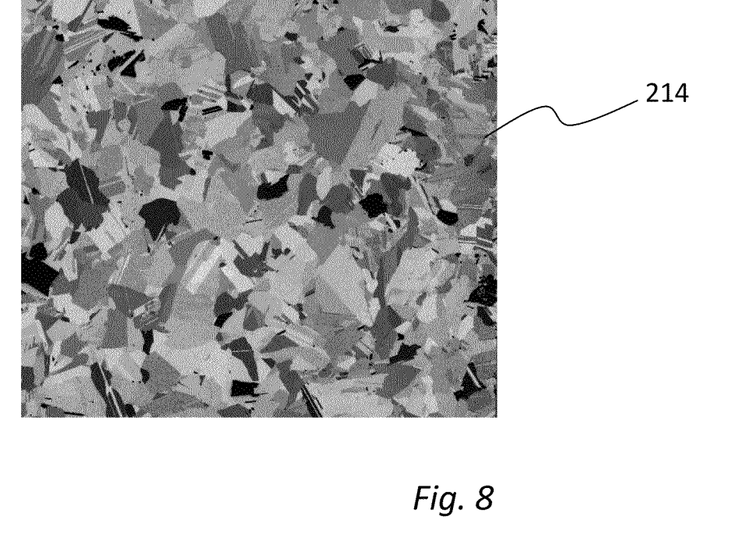
FIG. 8 is a two dimensional image of a semiconductor wafer surface generated from line data as disclosed herein.
Figure 9:
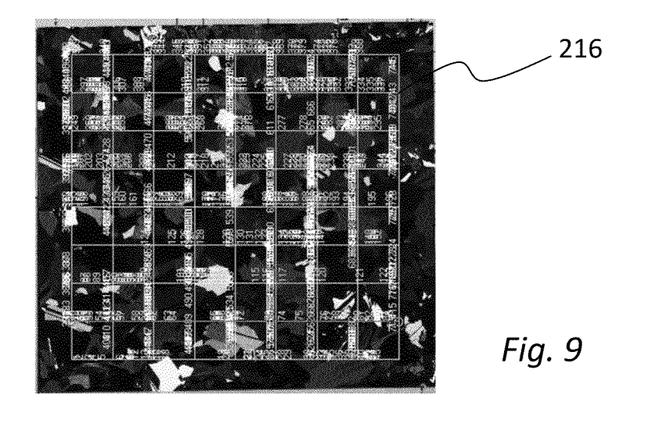
FIG. 9 is a two dimensional image of a semiconductor wafer surface generated from line data as disclosed herein with grid lines superimposed thereon to calculate crystal grain size.

It is possible to derive many parameters from the same data. For example, FIG. 8 is an image of a wafer 214 taken with a system 100 as described above with the wafer moving with respect to the line camera 106 at a rate of 5 inches per second. The data was acquired at a frame rate of 34 KHz and dynamically averaged as the wafer 214 moved through the monitoring zone. The two dimensional image of FIG. 8 was generated from data stored in an image storage mode, but the data could also have been monitored in a monitoring mode to detect irregularities as the wafer moved through the monitoring zone at production speeds. Each grey scale region shown on FIG. 8 uniquely represents one crystal orientation. Thus FIG. 8 is composited from data acquired line by line and processed to show crystalline grain size and crystalline grain orientation. As shown in FIG. 9, a grid 216 may be utilized to determine an average grain size and number of grains within a given region. Other parameters of interest may be calculated by adapting the methods and processes disclosed in U.S. Pat. No. 7,238,912 entitled Wafer Characteristics via Reflectometry and Wafer Processing Apparatus and Method and the disclosures of which reference is specifically incorporated herein for all teaching regarding the calculation of material parameters from image data.

Fuel Cell Membrane Process Monitoring

Membrane reflectance or transmittance data may be used to determine membrane thickness, defects, and generate two dimensional composition images as described above. In general, as the membrane web moves, the line camera continuously captures and registers data across the membrane width. The data processing system 110 may contemporaneously analyze the data and provide output or warnings if certain parameters are irregular. For example, if the membrane thickness is outside a prescribed range, the system can mark the irregular location or stop the web line.

With respect to fuel cell membranes, the system can detect reflected or transmitted light. Direct transmittance can advantageously be used for detecting or mapping variations in the porosity of electrodes, detecting or mapping absorbing or opaque defects such as streaks, or non-opaque defects such as pinholes. Oblique transmittance may be used to detect other parameters.

The local reflectance of a membrane can also be measured in two ways:

A. Direct (or specular) reflectance, using a single light source illuminating the web line at an oblique angle. Specular reflectance imaging is typically used for surface defects such as stains and absorbance imaging, which is useful for example in thickness mapping.

B. Scattered light imaging, using one or more than one symmetrically located light sources. Scattered light imaging is expected to be the typical mode of use. In a scattered light imaging implementation one or more illumination beams 121, typically projected at a shallow angle with respect to the planar surface of the fuel cell membrane, illuminate the web line as shown in FIG. 2 and line image data is collected along a line normal to the web surface.

Figure 10:
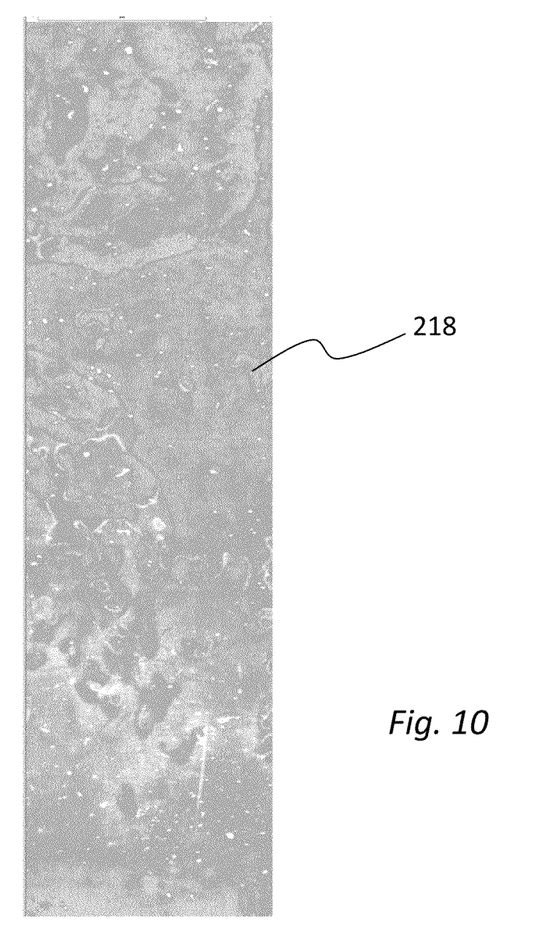
FIG. 10 is a two dimensional image of a fuel cell membrane surface generated from line data as disclosed herein.
Figure 11:
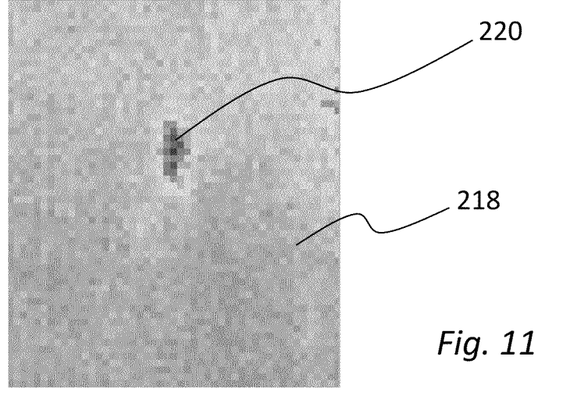
FIG. 11 is an enlarged two dimensional image of a fuel cell membrane defect generated from line data as disclosed herein.
Figure 12:
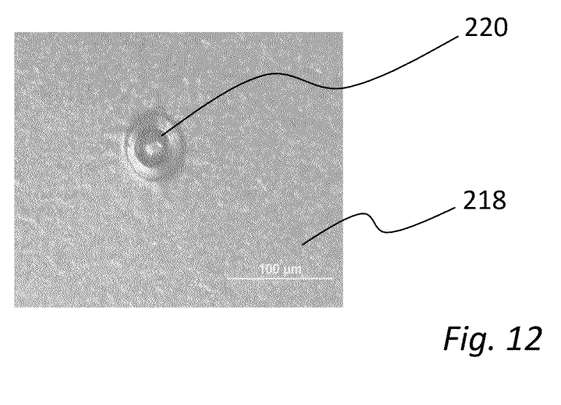
FIG. 12 is a microscope photograph image of the fuel cell membrane defect of FIG. 11.

FIG. 10 is a two dimensional image of a perfluorosulfonic acid (PFSA) fuel cell membrane 218 with data captured using a line camera and assembled into a two dimensional image using the system in an image storage mode as described above. Data was obtained using a device configuration similar to that illustrated in FIG. 2. The membrane was moving with respect to the line camera at a rate of 5 inches per second. The grey shades in FIG. 10 show defects in the membrane that arise from surface solidification and surface flow of liquid just prior to the solidification. The line data could be used in a monitoring mode to identify defects while the membrane is moving at production rates. For example, FIG. 11 is an enlarged view of a small portion of a membrane 218. FIG. 11 shows a very small bubble defect 220 in the membrane 218. The rendering of the defect 220 generated from line camera data captured while the membrane 218 was traveling at a production rate of speed (5 inches per second) may be compared to the FIG. 12 which shows a conventional microscope image of the same bubble defect 220 taken while the membrane was held stationary for microscopic inspection. Thus, the rendering of the defect 220 in FIG. 11 demonstrates that the described reflectance imaging system is capable of the identification of defects as the membrane travels at production speeds. As noted above, the data processing system can be configured to operate in a monitoring mode to alert a user of the presence of a defect such as defect 220 in near real time during membrane manufacture.

Figure 13:
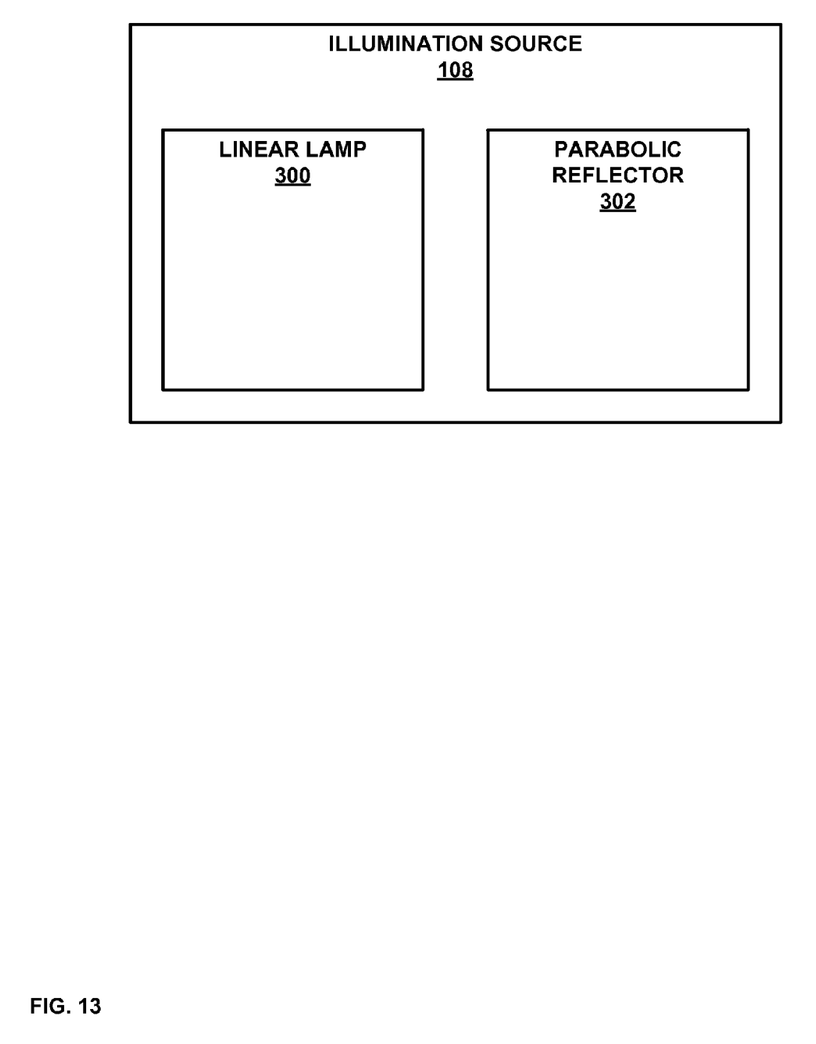
FIG. 13 is a block diagram illustrating one example of the illumination source shown in FIG. 1.

FIG. 13 is a block diagram illustrating one example of illumination source 108 shown in FIG. 1. As shown in the example of FIG. 13, illumination source 108 includes linear lamp 300 and parabolic reflector 302. Parabolic reflector 302 may provide for the projection of light toward the substantially planar material.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure. Several embodiments have been particularly shown and described. It should be understood by those skilled in the art that changes in the form and details may be made to the various embodiments disclosed herein without departing from the spirit and scope of the disclosure and that the various embodiments disclosed herein are not intended to act as limitations on the scope of the claims. Thus, while a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

What is claimed is:

1. A monitoring system comprising:
a material transport system configured to transport a substantially planar material through a monitoring zone of the monitoring system;
an illumination source positioned to illuminate the material with light that spans across a width of the material, wherein the light has substantially uniform intensity across the width of the material;
a line camera configured to obtain a plurality of consecutive line images, each comprising a respective linear array of pixels, wherein each consecutive line image captures non-specular reflections of the light from a respective section of the material, each respective section spanning the width of the material; and
a data processing system in digital communication with the line camera configured to:
receive, from the line camera, data representing each consecutive line image,
determine, based on the data representing each consecutive line image and for each of at least two pixels from the respective linear array of pixels, a respective value of a quality parameter of the material, and
output the respective value of the quality parameter of the material for each of the at least two pixels.

2. The monitoring system of claim 1, wherein the substantially planar material comprises one of a semiconductor wafer or a fuel cell membrane.

3. The monitoring system of claim 1, wherein the illumination source comprises:
a light source that generates the light;
a fiber optic providing for transmission of the light from the light source to a rectangular aperture; and
a lens in optical communication with the rectangular aperture.

4. The monitoring system of claim 1, wherein the illumination source comprises:
one of a linear array of LEDs or a linear lamp that generates the light and a parabolic reflector providing for projection of the light toward the substantially planar material.

5. The monitoring system of claim 1, wherein the illumination source is positioned with respect to the substantially planar material such that a line from the illumination source to the planar material forms an angle of less than 45° with a planar surface of the planar material.

6. The monitoring system of claim 1, wherein the illumination source comprises a source of polychromatic light having a range of wavelengths and wherein the monitoring system further comprises a filtering system, associated with the line camera, that is configured to transmit only selected wavelengths.

7. The monitoring system of claim 1, wherein the data processing system is configured to provide substantially contemporaneous data output regarding at least one of the following quality parameters: material surface roughness, material texture etch quality, anti-reflection coating thickness, wafer thickness, metallization quality, material back reflectance back layer thickness, crystalline grain size and crystalline grain orientation, membrane surface roughness, thickness values for different layers of a multiple-layer membrane, thickness of a single layer membrane, variations in porosity of the electrode-coated membrane, presence of absorbing defects, or presence of non-opaque defects.

8. The monitoring system of claim 1, further comprising one of an edge sensor, a position encoder, or a time regulated trigger providing for triggering of the line camera at selected time intervals.

9. The monitoring system of claim 1, wherein the data processing system is configured to provide substantially contemporaneous data output regarding at least one of the following quality parameters: membrane surface roughness, thickness values for different layers of a multiple-layer membrane, thickness of a single layer membrane, variations in porosity of the electrode-coated membrane, presence of absorbing defects, or presence of non-opaque defects.

10. The monitoring system of claim 1,
wherein the plurality of consecutive line images comprises a current line image and at least one previous line image, and wherein the data processing system is configured to determine the respective value of the quality parameter of the material for each of the at least two pixels from the respective linear array of pixels of the current line image further based on data representing the at least one previous line image.

11. The monitoring system of claim 10, wherein the data processing system is configured to determine the respective value of the quality parameter of the material for each of the at least two pixels from the respective linear array of pixels of the current line image by:
calculating, based on the data representing the at least one previous line image, an average value of the quality parameter;
calculating, based on data representing the current line image and for each of the at least two pixels from the respective linear array of pixels of the current line image, a respective current value of the quality parameter; and
comparing the respective current value of the quality parameter for each of the at least two pixels from the respective linear array of pixels of the current line image to the average value of the quality parameter.

12. The monitoring system of claim 1, wherein the illumination source comprises a first illumination source, and wherein the monitoring system further comprises a second illumination source positioned symmetrically opposite the first illumination source with respect to the line camera.

13. The monitoring system of claim 1, wherein the data processing system is configured to determine the respective value of the quality parameter of the material for each of the at least two pixels by:
generating, based on data representing at least two consecutive line images, a composite image of a portion of the material, and
calculating, based on the composite image, at least one of an average grain size, a grain orientation value, or a number of grains per unit area.

14. The monitoring system of claim 13, wherein the data processing system is configured to generate the composite image by generating a dynamic composite image, and wherein the data processing system is configured to calculate at least one of the average grain size, the grain orientation value, or the number of grains per unit area by calculating, based on the dynamic composite image, a rolling value of at least one of the average grain size, the average grain orientation value, or the average number of grains per unit area.

15. The monitoring system of claim 1, wherein the data processing system is further configured to:
determine a respective value of the quality parameter of the material for each pixel from the respective linear array of pixels for a plurality of consecutive line images; and
output, based on the respective value of the quality parameter of the material for each pixel from the respective linear array of pixels for the plurality of consecutive line images, a two-dimensional mapping of the quality parameter of the material.

16. A method of monitoring a material, the method comprising:
transporting a substantially planar material through a monitoring zone of a monitoring system;
illuminating, by an illumination source, the material with light that spans across a width of the material, wherein the light has substantially uniform intensity across the width of the material;
obtaining, by a line camera, a plurality of consecutive line images, each comprising a respective linear array of pixels, wherein each consecutive line image captures non-specular reflections of the light from a respective section of the material, each respective section spanning the width of the material; and
calculating, by a data processing system in digital communication with the line camera, based on data representing each consecutive line image, and for each of at least two pixels from the respective linear array of pixels, a respective value of a quality parameter of the material.

17. The method of monitoring a material of claim 16, further comprising comparing the respective value of the quality parameter of the material for each of the at least two pixels with a standard parameter value.

18. The method of monitoring a material of claim 16, further comprising identifying an irregularity in the material based upon the respective value of the quality parameter of the material for at least one of the at least two pixels.

19. The method of monitoring a material of claim 16, wherein the illumination source comprises:
a light source that generates the light;
a fiber optic providing for transmission of the light from the light source to a rectangular aperture; and
a lens in optical communication with the rectangular aperture.

20. The method of monitoring a material of claim 16, wherein the illumination source comprises:
one of a linear array of LEDs or a linear lamp that generates the light and a parabolic reflector providing for projection of the light toward the substantially planar material.

21. The method of monitoring a material of claim 16, wherein the illumination source is positioned with respect to the substantially planar material such that a line from the illumination source to the planar material forms an angle of less than 45° with a planar surface of the planar material.

22. The method of monitoring a material of claim 16, wherein the illumination source is positioned opposite the substantially planar material from the line camera.

23. The method of monitoring a material of claim 16, wherein the illumination source comprises a source of polychromatic light having a range of wavelengths and wherein obtaining the plurality of line images comprises capturing only light having selected wavelengths.

24. The method of monitoring a material of claim 16, wherein the data processing system calculates values of at least one of the following quality parameters; material surface roughness, material texture etch quality, anti-reflection coating thickness, wafer thickness, metallization quality, material back reflectance back layer thickness, crystalline grain size and crystalline grain orientation, membrane surface roughness, thickness values for different layers of a multiple-layer membrane, thickness of a single layer membrane, variations in porosity of the electrode-coated membrane, presence of absorbing defects, or presence of non-opaque defects.

* * * * *